United States Patent
Kroll et al.

(10) Patent No.: US 7,272,438 B2
(45) Date of Patent: Sep. 18, 2007

(54) MODE SWITCHING HEART STIMULATION APPARATUS AND METHOD

(75) Inventors: Mark W. Kroll, Crystal Bay, MN (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 99 days.

(21) Appl. No.: 10/964,226

(22) Filed: Oct. 12, 2004

(65) Prior Publication Data

US 2007/0156191 A1    Jul. 5, 2007

(51) Int. Cl.
 *A61B 5/0464*    (2006.01)
(52) U.S. Cl. .................... 600/518; 600/515; 607/14; 607/15
(58) Field of Classification Search ............ 607/14, 607/15; 600/515, 518
See application file for complete search history.

(56) References Cited

U.S. PATENT DOCUMENTS

| | | | | |
|---|---|---|---|---|
| 4,603,705 A | 8/1986 | Speicher et al. | ............ | 128/786 |
| 4,712,555 A | 12/1987 | Thornander et al. | .. | 128/419 PG |
| 4,788,980 A | 12/1988 | Mann et al. | .......... | 128/419 PG |
| 4,940,052 A | 7/1990 | Mann et al. | .......... | 128/419 PG |
| 4,944,298 A | 7/1990 | Sholder | ................ | 128/419 PG |
| 5,466,254 A | 11/1995 | Helland | ....................... | 607/123 |
| 5,476,483 A | 12/1995 | Bornzin et al. | ................ | 607/17 |
| 5,522,855 A | 6/1996 | Hoegnelid | ..................... | 607/9 |
| 5,540,727 A | 7/1996 | Tockman et al. | .............. | 607/18 |
| 5,800,465 A * | 9/1998 | Thompson et al. | ............ | 607/9 |
| 5,843,133 A * | 12/1998 | Routh et al. | ................... | 607/14 |
| 6,285,906 B1 * | 9/2001 | Ben-Haim et al. | .............. | 607/4 |
| 6,370,427 B1 | 4/2002 | Alt et al. | ......................... | 607/4 |
| 6,477,417 B1 | 11/2002 | Levine | ........................... | 607/9 |
| 6,477,420 B1 | 11/2002 | Struble et al. | ................ | 607/14 |
| 6,609,027 B2 | 8/2003 | Kroll et al. | ..................... | 607/9 |
| 6,628,988 B2 * | 9/2003 | Kramer et al. | ................. | 607/9 |
| 6,701,186 B2 * | 3/2004 | Spinelli et al. | ................ | 607/9 |
| 6,934,586 B2 * | 8/2005 | Struble et al. | ................ | 607/23 |
| 2002/0082660 A1 | 6/2002 | Stahmann et al. | ............ | 607/14 |
| 2002/0091333 A1 | 7/2002 | Hsu et al. | .................... | 600/518 |
| 2002/0193834 A1 | 12/2002 | Levine | ........................... | 607/9 |
| 2003/0069610 A1 * | 4/2003 | Kramer et al. | ................. | 607/25 |
| 2003/0199928 A1 | 10/2003 | Hsu et al. | ....................... | 607/5 |

FOREIGN PATENT DOCUMENTS

| | | |
|---|---|---|
| WO | WO 01/30436 A2 | 5/2001 |
| WO | WO 03/037177 A2 | 5/2003 |
| WO | WO 03/037177 A3 | 5/2003 |

* cited by examiner

*Primary Examiner*—Carl Layno
*Assistant Examiner*—Yun Haeng Lee

(57) ABSTRACT

In a heart stimulation device a mode of operation is switched in response to detection of atrial tachyarrhythmia such as atrial fibrillation. The stimulation device may initially operate in a normal mode of pacing then, upon detection of atrial tachyarrhythmia, the stimulation device may change how it senses signals and it may switch to another mode of pacing at one or more sites in the ventricle.

20 Claims, 9 Drawing Sheets

MODE SWITCHING HEART STIMULATION APPARATUS AND METHOD

TECHNICAL FIELD

This application relates generally to implantable cardiac stimulation devices and, more specifically, to a stimulation apparatus and method that switches modes of operation based on detection of atrial tachyarrhythmia in an effort to maintain cardiac resynchronization therapy.

BACKGROUND

A conventional pacemaker stimulates a patient's heart to maintain regular contractions of the heart thereby promoting blood circulation within the patient. Such stimulation may be prescribed when the patient's heart does not function normally due to, for example, a genetic or acquired condition involving the sinus node or AV conduction system resulting in a symptomatic bardycardia.

In a healthy heart, contractions occur first in the muscles associated with the atrial chambers of the heart, followed by contractions in the muscles associated with the larger ventricular chambers of the heart. In this way, the atria assist in the filling of the ventricular chambers with blood returning from the veins. This increases the end-diastolic volume increasing the stroke volume to enable the ventricles to more efficiently pump blood to the arteries.

Given the interaction of these chambers, efficient operation of the heart is predicated on each of the chambers operating in a proper timing sequence and having contractions that pump a sufficient amount of blood from the chamber. For example, during contraction the right atrium chamber should pump enough blood to optimally "fill" the right ventricle chamber. Moreover, this should occur immediately before the right ventricle begins to contract. In this way, the heart may efficiently pump blood on a repetitive basis.

A healthy heart repetitively contracts in the above described manner in response to the generation and conduction of electrical signals in the heart. These electrical signals are generated in and conducted through the heart during every beat of the heart. A simplified example of these electrical signals follows.

Activity for a given beat begins with the generation of a signal in a sinus node of the heart. This signal causes contraction to begin first in the atria. The signal from the sinus node propagates via a conduction system to an atrio-ventricular ("A-V") node. The signal is delayed for a very short period of time (usually less than 200 ms) within the AV node allowing the atria to contract to help to fill the ventricles. The signal then propagates from the A-V node through the bundle of His to the left and right ventricles via a specialized conduction system. Contraction in each ventricle commences in a coordinated manner when the signal "reaches" the respective muscle fibers in the ventricle.

In a diseased or otherwise unhealthy heart, there may be a disruption or abnormality in the generation and/or propagation of these signals. For example, in some patients the atria may generate signals in a sporadic manner or there may be a blockage that prevents the signal from the sinus node from reaching the ventricles in a normal manner. In either of these cases, the atrial-ventricular timing may be compromised resulting in inefficient operation or failure of the heart. In other patients, the activation of the main pumping chamber, the left ventricle, is abnormal compromising the coordination of left ventricular contraction and thus compromising cardiac efficiency.

Under certain circumstances, a pacemaker may compensate for abnormal operation of a heart by pacing (e.g., stimulating) one or more of the atria and/or ventricles. To stimulate the heart, a typical pacemaker generates a series of electrical signals which are applied to the heart via one or more electrodes implanted in the heart (e.g., in ventricular or atrial chambers). These electrical signals cause the heart to contract in much the same way as the native electrical signals discussed above cause the heart to contract.

To provide appropriate timing for the generation of electrical signals, conventional pacemakers may sense signals in the heart. For example, when a heart has a functioning sinus node but has some form of a blockage between the sinus node and the ventricles, a pacemaker may sense electrical signals in the atria to detect when the atria are being activated. The pacemaker may then delay a prescribed period of time after which it applies a stimulus to the ventricles. In this way, the pacemaker may stimulate the ventricles at the appropriate time in an attempt to maintain efficient operation of the heart.

In recent years, it has been recognized that patients with congestive heart failure due to a mechanical problem with the heart muscle may develop a delay in conduction through the left ventricle further compromising overall cardiac function. This is identified on a surface electrocardiogram (ECG) by a widening of the electrical signal from the ventricle (QRS complex) with a pattern known as intraventricular conduction delay (IVCD) or abnormality, the most common of which is left bundle branch block ("LBBB"). In an effort to restore or improve the coordination of the cardiac contraction, two ventricular leads are being utilized, one placed in the right ventricle to stimulate the left ventricular septum and one advanced through the coronary sinus to stimulate the posterior or lateral wall of the left ventricle via a lead located in a cardiac vein. A transthoracic epicardial lead can achieve a similar result. By stimulating both ventricular leads at the same time or in a specified sequence, resynchronization of the left ventricular contraction pattern can be achieved to improve overall cardiac function. Many patients for whom CRT therapy is recommended do not have sinus node dysfunction or AV block.

Many patients with CHF may suffer from a condition known as atrial tachyarrhythmia. This condition may result in sporadic signals being passed through the A-V node which may cause sporadic activation of the ventricles. More importantly, they compromise ventricular filling by compromising the atria's ability to contract in a coordinated manner. As a result, the ventricles may function in a less efficient or ineffective manner in such patients. A standard DDD pacemaker, if it had been implanted for either AV block or sinus node dysfunction, may track these abnormal atrial signals driving the ventricle at a physiologically inappropriate and rapid rate further compromising ventricular function. Automatic mode switch (AMS) algorithms have been developed to recognize the pathologically rapid atrial rates and convert the pacemaker from a tracking to a nontracking mode. In a patient with a CRT stimulation system who does not have a primary need for pacing therapy, development of a pathologic atrial tachyarrhythmia not only forces a loss of AV synchrony and a generally rapid ventricular rate, it also results in the loss of cardiac resynchronization that was the result of the implanted multisite stimulation system.

Pacing techniques have been proposed for managing the implanted device's response to pathologic atrial tachyarrhythmias that have a standard need for pacing therapy. There is a need for more effective techniques for treating patients with atrial tachyarrhythmia who also have congestive heart failure, a disordered ventricular activation sequence associated with intrinsic conduction and in whom multisite ventricular pacing is being utilized in an attempt to restore a left ventricular synchronized contraction pattern. In the presence of standard automatic mode switching algorithms (AMS), switching to a nontracking mode in the presence of an atrial tachyarrhythmia results in the loss of cardiac resynchronization therapy ("CRT").

SUMMARY

What is described herein is an apparatus for, and method of, pacing (e.g., stimulating) a heart where one or more modes of operation may be changed in response to detection of atrial tachyarrhythmia in patients with congestive heart failure in whom a multisite ventricular stimulation system (pacemaker or ICD) has been implanted. For example, some embodiments of a stimulation device (e.g., pacemaker) constructed in accordance with the invention may initially operate in a normal mode of pacing then, upon detection of atrial tachyarrhythmia, the stimulation device may change how it responds to detected atrial signals and it may switch to another mode of pacing. For convenience, an embodiment of a stimulation device constructed according to the invention will be referred to herein simply as an "embodiment."

In some embodiments, after detecting atrial tachyarrhythmia, the stimulation device uses a global sensing technique to sense electrical signals from either or both ventricular chambers of the heart. For example, the sensor or sensors used by the stimulation device may be configured to sense over a relatively wide area of the heart. By sensing over a relatively large area, the stimulation device may be able to more effectively detect the earliest onset of ventricular activation. This, in turn, may enable the stimulation device to effectively pace multiple sites in the ventricle before the left ventricle is completely activated.

In some embodiments the stimulation device senses global signals using a unipolar electrode. For example, the stimulation device may parallel ventricle tip and ring electrodes to detect ventricular activation. The stimulation device may reference the paralleled tip and ring signal to the stimulation device "can." Alternatively, the paralleled tip and ring signal may be referenced to a left ventricle signal.

After detecting an atrial tachyarrhythmia, the mode changes from a tracking to a nontracking mode. In the absence of spontaneous AV nodal conduction, the stimulation device generates pacing signals to pace the left ventricle and/or right ventricle. In some embodiments when AV nodal conduction is intact, the stimulation device simultaneously sends pacing signals to both the right ventricle and the left ventricle or multiple ventricular sites after detecting early ventricular activation. Here, provided ventricular activation is detected soon enough, the stimulation device may be able to effectively pace a ventricle where activation has not commenced. As a result, the stimulation device may provide cardiac synchronization in the setting of spontaneous intact AV nodal conduction.

Some embodiments may operate in one of two modes after the stimulation device detects atrial tachyarrhythmia. For example, if the stimulation device is capable of sensing signals at, for example, the bundle of His or at the interventricular septum, the stimulation device may select a mode of pacing where the stimulation device first paces the left ventricle then, after a delay period, the stimulation device paces the right ventricle before the native conduction would reach either of these chambers. If, on the other hand, the stimulation device is not sensing the bundle of His or the septum, the stimulation device may use another sensor to detect signals that are processed to detect early ventricular activation. In this latter case, the stimulation device may pace the ventricles as discussed above.

In some embodiments, after detecting atrial tachyarrhythmia, the stimulation device filters the sensed ventricle signals using one or more specifically selected filters. For example, a filter may be selected with a relatively broad bandwidth so that the stimulation device may effectively sense relatively low frequency and/or low amplitude signals that may emanate from early ventricular activation.

In some embodiments the stimulation device's normal mode of operation provides multisite ventricular pacing that is triggered by detection of an atrial beat. Thus, the normal mode of pacing may include delaying after detecting of the atrial beat then stimulating the left ventricle, delaying again then stimulating the right ventricle. The stimulation device includes circuitry and/or software to detect an atrial tachyarrhythmia such as atrial fibrillation. In response to a detection of atrial tachyarrhythmia, the stimulation device changes its mode of both a response to the abnormal atrial rhythm and sensing of ventricular activation so that it may effectively detect the very earliest manifestations of ventricular activation and rather than inhibit the stimulation output, cause the implanted device to trigger an output to one or more electrodes positioned in the ventricles. In addition, the stimulation device changes its mode of multisite ventricular pacing so that once ventricular activation is detected the stimulation device either simultaneously paces through its various ventricular leads or selectively delivers stimuli to specific ventricular leads. In this way, the stimulation device may provide synchronization that counteracts the effect of rapid atrial signals that may trigger AMS but at the same time, be conducted from the atria to the ventricles resulting in the loss of cardiac resynchronization.

BRIEF DESCRIPTION OF THE DRAWINGS

These and other features, aspects and advantages of the invention will be more fully understood when considered with respect to the following detailed description, appended claims and accompanying drawings, wherein:

Figure 1:
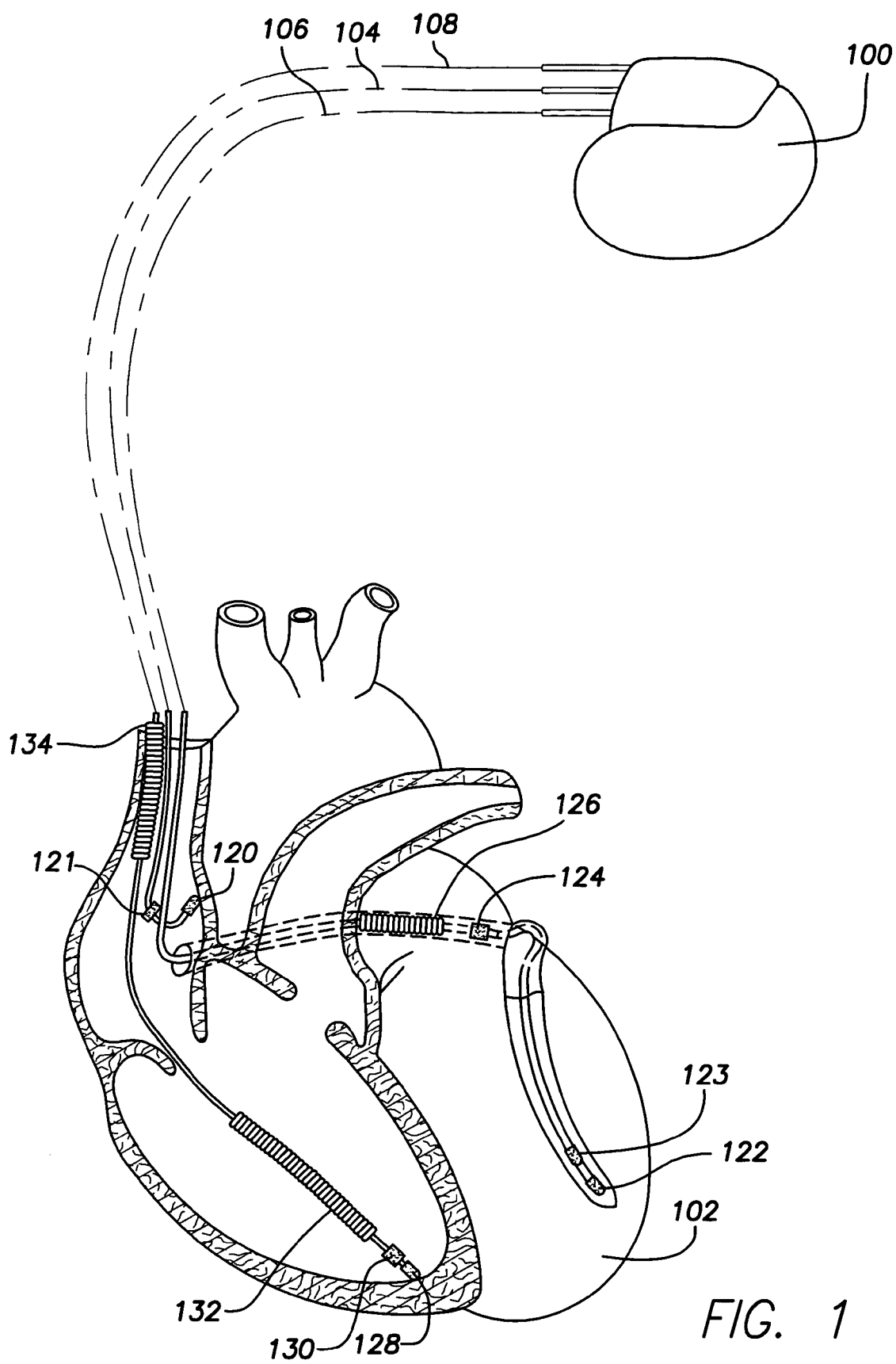
FIG. 1 is a simplified diagram of one embodiment of an implantable stimulation device in electrical communication with at least three leads implanted in a patient's heart for delivering multi-chamber stimulation and shock therapy in accordance with the invention.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals denote like features throughout the specification and figures.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed herein are merely representative and do not limit the scope of the invention.

Exemplary Stimulation Device

The following description sets forth but one exemplary stimulation device that is capable of being used in connection with the various embodiments that are described below. It is to be appreciated and understood that other stimulation devices, including those that are not necessarily implantable, can be used and that the description below is given, in its specific context, to assist the reader in understanding, with more clarity, the inventive embodiments described herein.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage or septum. FIG. 1 shows the right atrial lead 104 as having an optional atrial ring electrode 121.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 122, left ventricular ring electrode 123, left atrial pacing therapy using at least a left atrial ring electrode 124, and shocking therapy using at least a left atrial coil electrode 126 (or other electrode capable of delivering a shock). For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132 (or other electrode capable of delivering a shock), and superior vena cava (SVC) coil electrode 134 (or other electrode capable of delivering a shock). Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

In some embodiments, improvements in therapy may be achieved by stimulating the patient at two, three or more sites. For example, multiple electrodes may be implanted in the left ventricle. This technique may be referred to as multisite stimulation.

Figure 2:
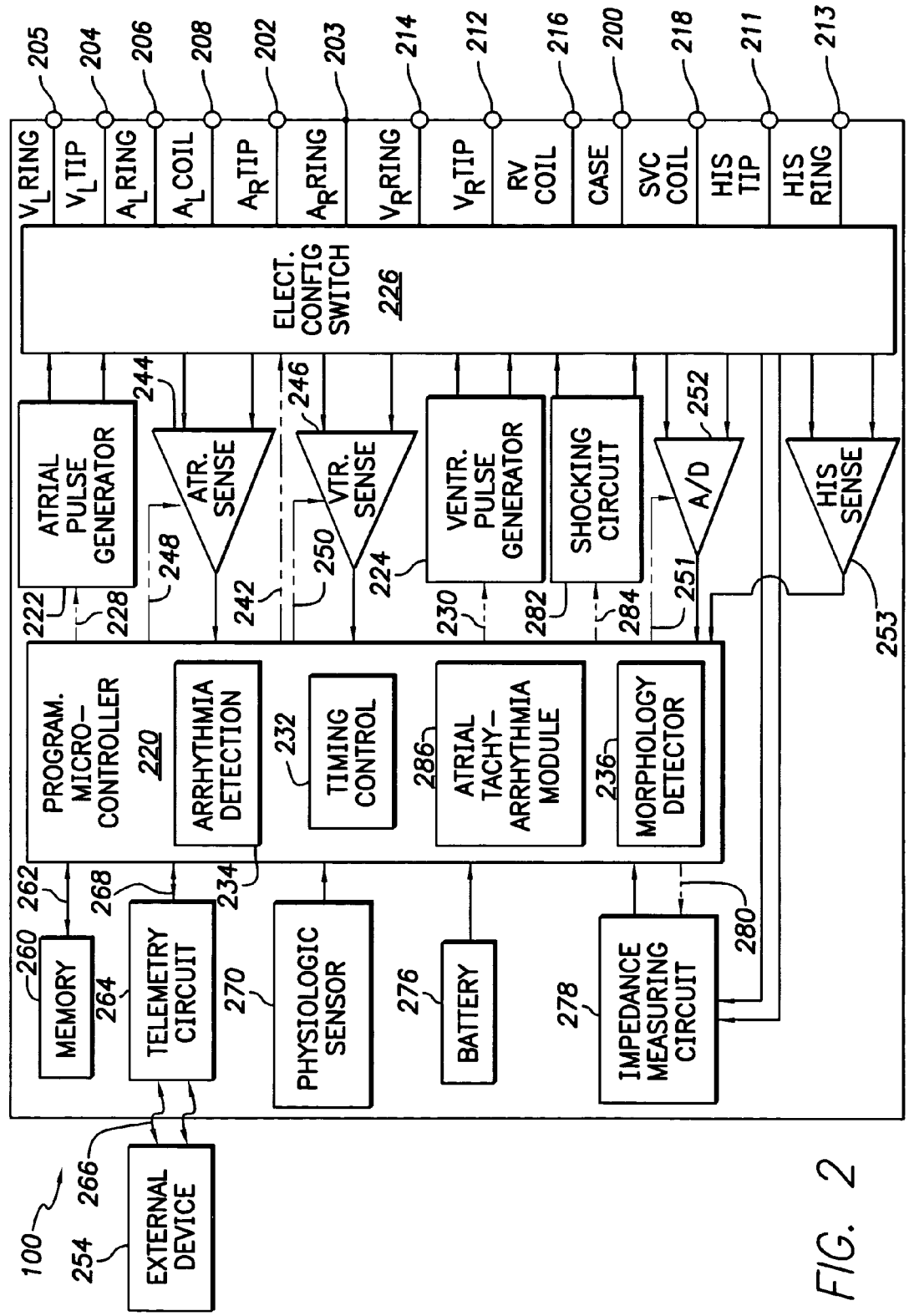
FIG. 2 is a simplified functional block diagram of one embodiment of a multi-chamber implantable stimulation device constructed in accordance with the invention, illustrating basic elements that are configured to provide cardioversion, defibrillation or pacing stimulation or any combination thereof.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal (AR TIP) 202 adapted for connection to the atrial tip electrode 120. A right atrial ring terminal (AR RING) 203 may also be included adapted for connection to the atrial ring electrode 121. To achieve left chamber sensing, pacing, and shocking, the connector includes at least a left ventricular tip terminal (VL TIP) 204, left ventricular ring terminal (VL RING) 205, a left atrial ring terminal (AL RING) 206, and a left atrial shocking terminal (AL COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured (e.g., via signal line 251) to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors to help detect movement and minute ventilation in the patient. The physiological sensors 270 may include but are not limited to a position sensor and/or minute ventilation (MV) sensor to detect minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 100 preferably employs lithium.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 to 2.0 J), moderate (e.g., 2.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, and/or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Atrial Tachyarrhythmia Mode Switching

Microcontroller 220 may include an atrial tachyarrhythmia module 286 for performing a variety of tasks related to detection of atrial tachyarrhythmia and configuring the stimulation device 100. For example, the module 286 may filter and process received atrial signals to detect atrial tachyarrhythmia. In response to the detection of atrial tachyarrhythmia the module 286 may select modes of sensing and modes of pacing to be used by the stimulation device 100. In addition, the module 286 may process other sensed signals in conjunction with the operation of the selected modes. In general, the module 286 typically includes software and/or hardware for performing the above operations. The operation of the module 286 and other components of FIGS. 1 and 2 are described in more detail below.

Patients who suffer from congestive heart failure may be treated using a cardiac resynchronization device that helps to synchronize the ventricular contraction pattern. Typically, these patients have a functioning A-V node. Thus, electrical signals generated in the patient's atria may propagate through the A-V node to the ventricles. In the usual CRT situation, multisite ventricular stimulation is triggered in response to sensed atrial events at an interval that allows the implanted system to usurp control of the normal AV nodal conduction system before intrinsic AV nodal conduction can occur.

When such a patient's heart goes into atrial fibrillation or other pathologic atrial tachyarrhythmia, the atria may generate electrical signals at an abnormally high rate. Some of these signals may pass through the A-V node to the ventricles. The introduction of these signals in the ventricles may, in turn, minimize or eliminate synchronization within the left ventricle even while the tracking mode is still in effect. When AMS is engaged, the loss of tracking results in near total control of ventricular activation by the native conduction system. As a result, the ventricle may contract both in an irregular manner and due to the native intraventricular conduction abnormality thereby exacerbating low cardiac output.

Figure 3:
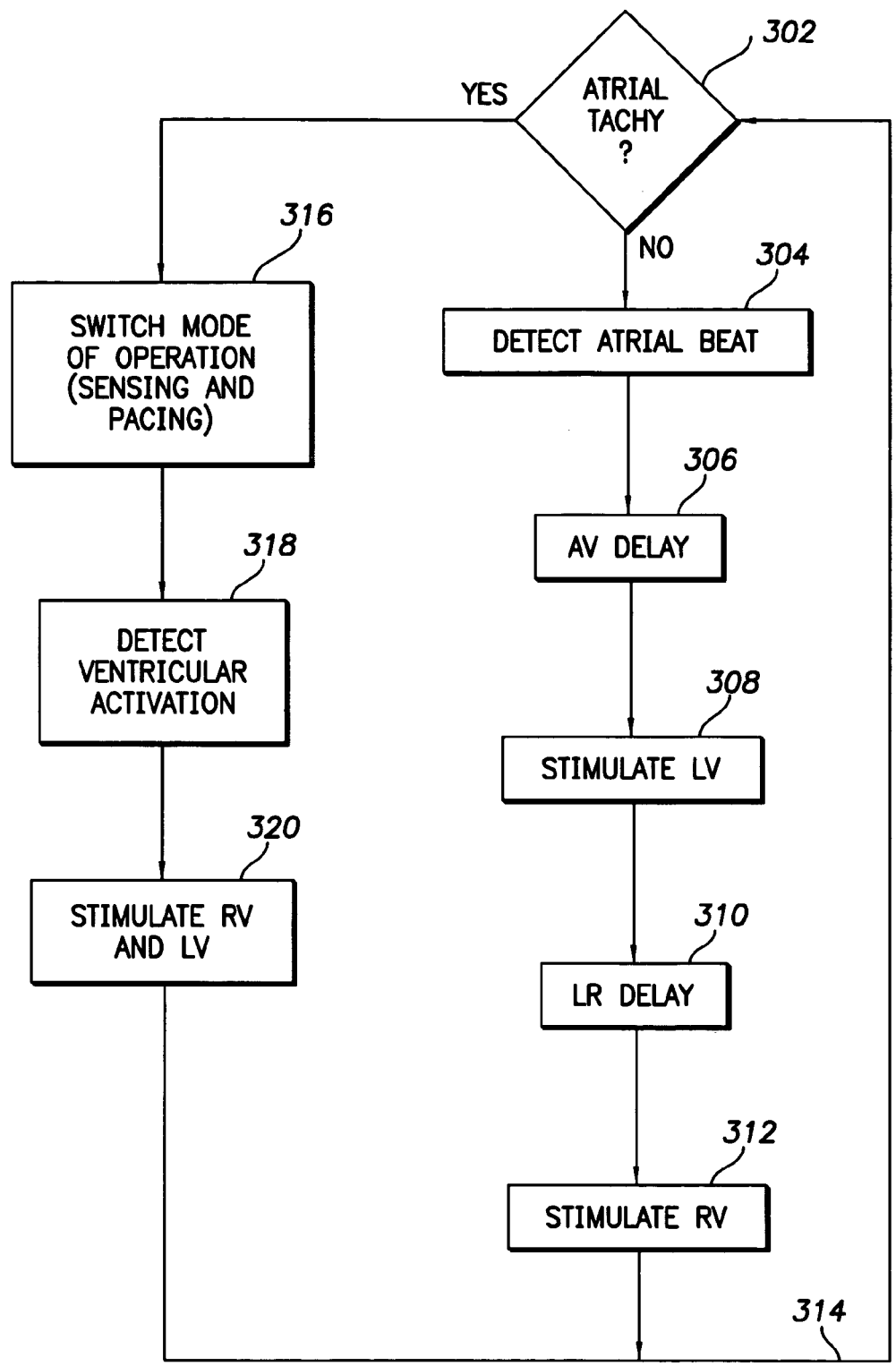
FIG. 3 is a simplified flow chart of one embodiment of operations that may be performed in accordance with the invention.

FIG. 3 is a flowchart illustrating one embodiment of operations that may be performed by the stimulation device 100 to counteract the effects of atrial tachyarrhythmia such as atrial fibrillation, atrial flutter or atrial tachycardia. In this embodiment, a multisite ventricular mode of pacing has been prescribed as the patient's normal mode of pacing.

As represented by block 302, the stimulation device 100 may monitor signals from the patient to determine whether the patient's heart is experiencing some form of atrial tachyarrhythmia such as atrial fibrillation.

The stimulation device 100 detects atrial tachyarrhythmia by monitoring signals from the heart. For example, in some embodiments the stimulation device 100 monitors signals sensed by one or more atrial electrodes. As depicted in FIG. 1, the stimulation device 100 may monitor right atrium tip-to-ring signals (via electrodes 120 and 121), right atrium tip-to-can signals (via electrode 120 and can 100), left atrium ring-to-can signals (via electrode 124 and can 100) or some combination of these signals. It should be appreciated that other methods may be used to sense signals that indicate atrial tachyarrhythmia.

The stimulation device 100 continually processes the sensed signals to determine whether the heart is currently experiencing atrial tachyarrhythmia. Typically, the stimulation device periodically samples and processes the sensed signals. As discussed above, the sensed signals may be amplified, filtered and sampled by the atrial sensing circuit 244. The controller 220 (e.g., arrhythmia detection 234 and/or atrial tachyarrhythmia module 286) processes the signals to detect atrial tachyarrhythmia. For example, as discussed above the controller 220 may analyze timing intervals between sensed events and classify the sensed signals according to defined limits. The controller 220 also may use other techniques to detect atrial tachyarrhythmia from sensed signals.

If atrial tachyarrhythmia is not detected at block 302, the stimulation device 100 provides the normal mode of pacing as described in blocks 304-312. Briefly, the stimulation device 100 first monitors atrial signals to detect an atrial beat (block 304). Then, as represented by block 306, the stimulation device 100 delays for a defined period of time to enable the atria to assist in the filling of the ventricles. Typically, this delay period is defined to be shorter than the time between the patient's normal atrial contraction and ventricular activation under given circumstances.

As represented by blocks 308-312, the stimulation device 100 stimulates the left ventricle, delays for an appropriate period of time, then stimulates the right ventricle. As represented by line 314, the process defined by blocks 302-312 is repeated every beat cycle.

If atrial tachyarrhythmia is detected at block 302, the controller 220 may change the mode of operation of the stimulation device 100 (block 316). To this end, the controller may immediately transfer processing to an application routine that handles processing for atrial tachyarrhythmia. The transfer of processing also may be accomplished by generating a signal (e.g., an interrupt signal) that indicates atrial tachyarrhythmia has been detected. In this case, the interrupt may cause immediate execution of the application routine for handling atrial tachyarrhythmia. Alternatively, the controller may set a status indication (e.g., a flag in data memory 260) that indicates atrial tachyarrhythmia has been detected. In this case, the indication may be read by, for example, a pacing routine generates the pacing signals for each heart beat. In this case, at the beginning of each beat the pacing routine may check the indication to determine which mode of operation applies to the current beat.

In some embodiments, the stimulation device 100 may change the way it senses signals to provide appropriate therapy during atrial tachyarrhythmia. For example, the stimulation device 100 may be reconfigured to detect ventricular activation (e.g., depolarization) as a precursor for stimulating the ventricles. Here, it is desirable to pace the ventricles as soon as possible after the onset of ventricular activation. If the stimulation is applied too late in the cycle both ventricles will be in a refractory state and the stimulation will be ineffective.

Figure 4:
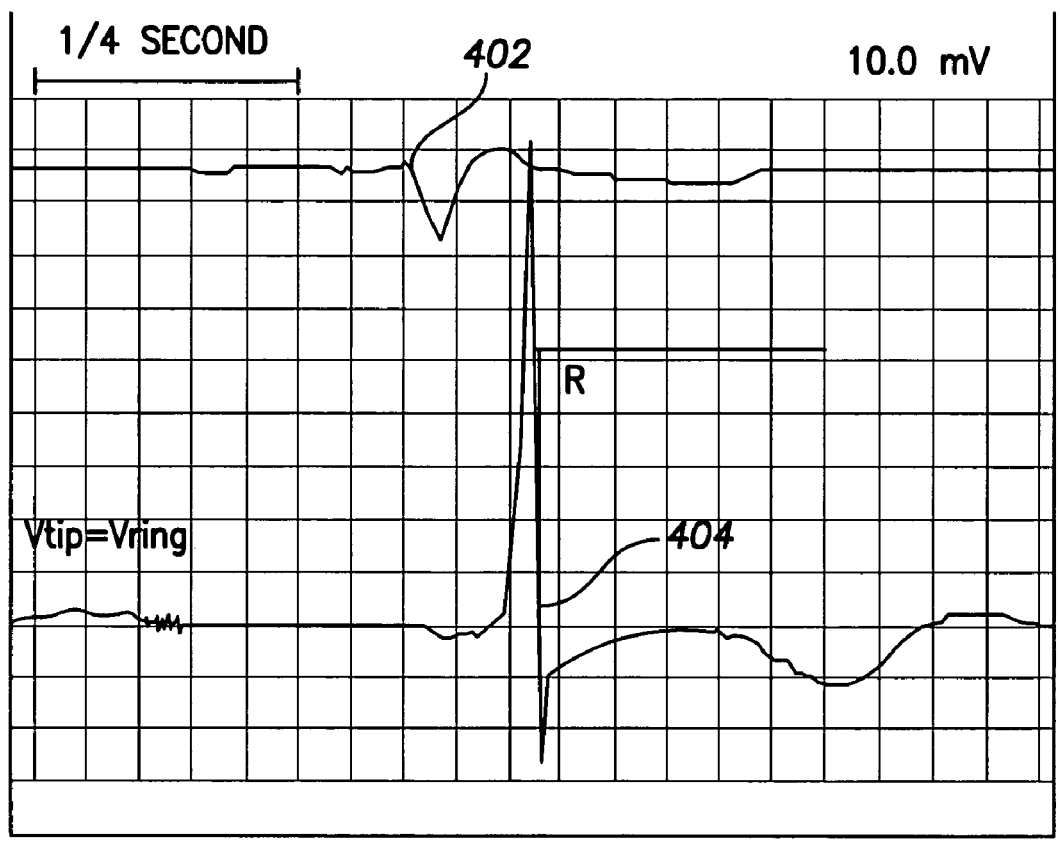
FIG. 4 is a signal trace diagram depicting one example of the intracardiac signal associated with a single ventricular lead located in the right ventricle.

FIG. 4 is a representation of an R wave and a signal that the stimulation device 100 may receive from, for example, a conventional bipolar ventricle tip-to-ring electrode. In particular, FIG. 4 illustrates the delay between the onset of ventricular activation (signal 402) and the time at which the electrode senses ventricular activity (signal 404). The delay occurs, in part, because bipolar electrodes typically are designed to sense in a relatively focused area. That is, the electrodes sense areas that are relatively close to the electrodes. As a result, the electrodes may not sense the earliest activation of the ventricles when such activation occurs in a portion of the ventricles that is relatively far from the electrodes. Rather, these electrodes will sense activation after the activation process progresses through the ventricles and activates a portion of the ventricles near the electrodes.

In one embodiment the stimulation device 100 uses a global sensing technique to detect the onset of ventricular activation. That is, the stimulation device 100 uses sensors (e.g., electrodes) that sense over a relatively large area. In this way, the stimulation device 100 may be able to sense activation that occurs in essentially any part of the ventricles. As a result, the stimulation device 100 may detect the signal generated by the portion of the ventricles that is first activated.

As an example, in some embodiments the stimulation device 100 senses bipolar signals from the right ventricle tip-to-ring electrodes during a normal mode of operation. After atrial tachyarrhythmia has been detected, the stimulation device 100 switches to a different electrode configuration (e.g., a unipolar electrode) that detects signals over a larger area. In this way, earlier ventricular activation signals may be sensed. A variety of electrode configurations may be used to sense global signals. Several examples follow.

Figure 5:
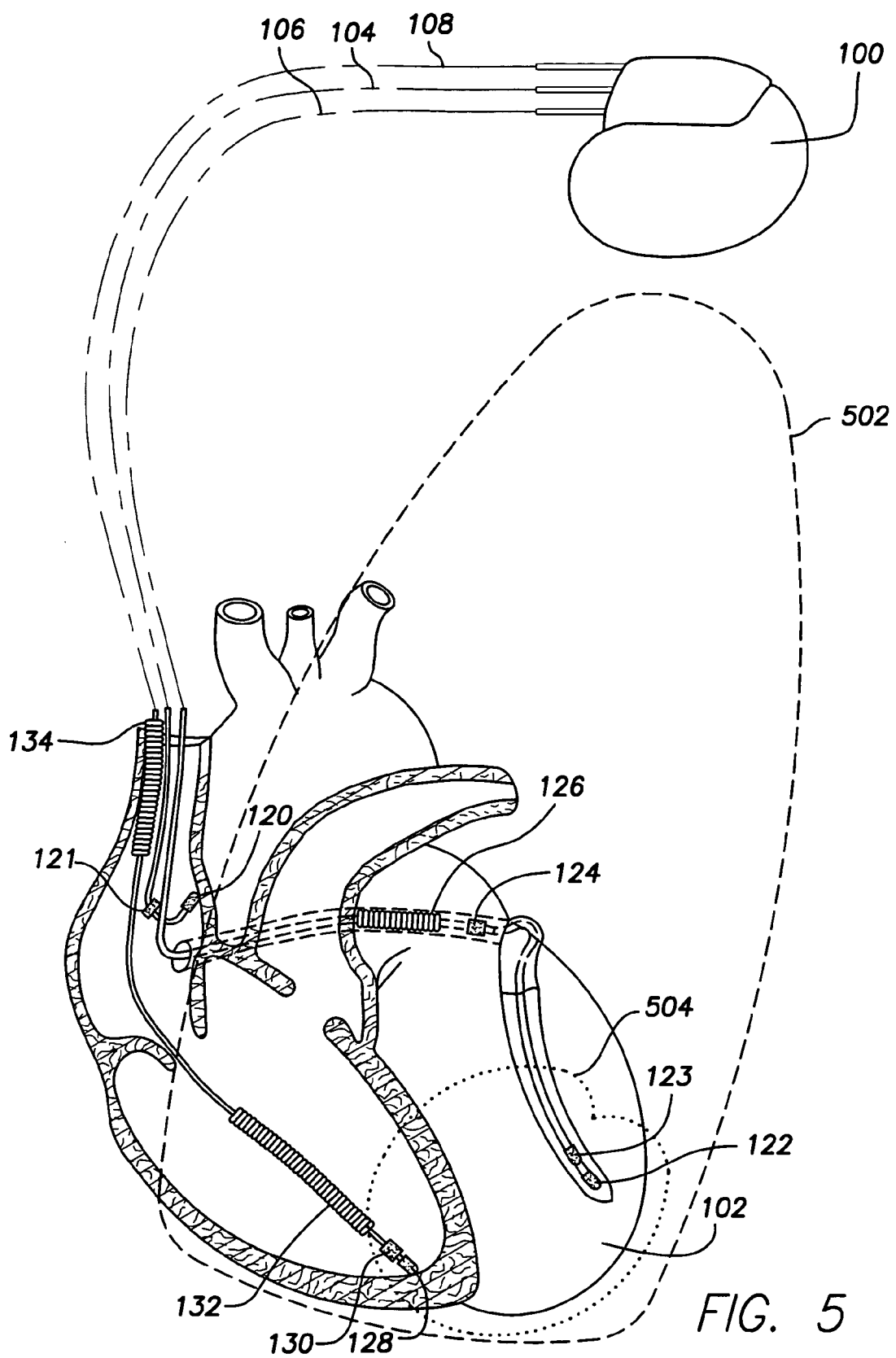
FIG. 5 is a simplified diagram depicting one embodiment of wide field signal sensing in accordance with the invention.

Some embodiments generate a global signal using unipolar signals generated by, for example, a right ventricle tip-to-can electrode configuration or a left ventricle tip-to-can electrode configuration. FIG. 5 illustrates a simplified example of a field pattern 502 that represents an area within which a right ventricle tip-to-can electrode configuration may sense signals. The drawing illustrates that signals may be sensed over a large portion or the entirety of the ventricles. The actual field pattern used in a given application may be adjusted using known sensing techniques.

Figure 6:
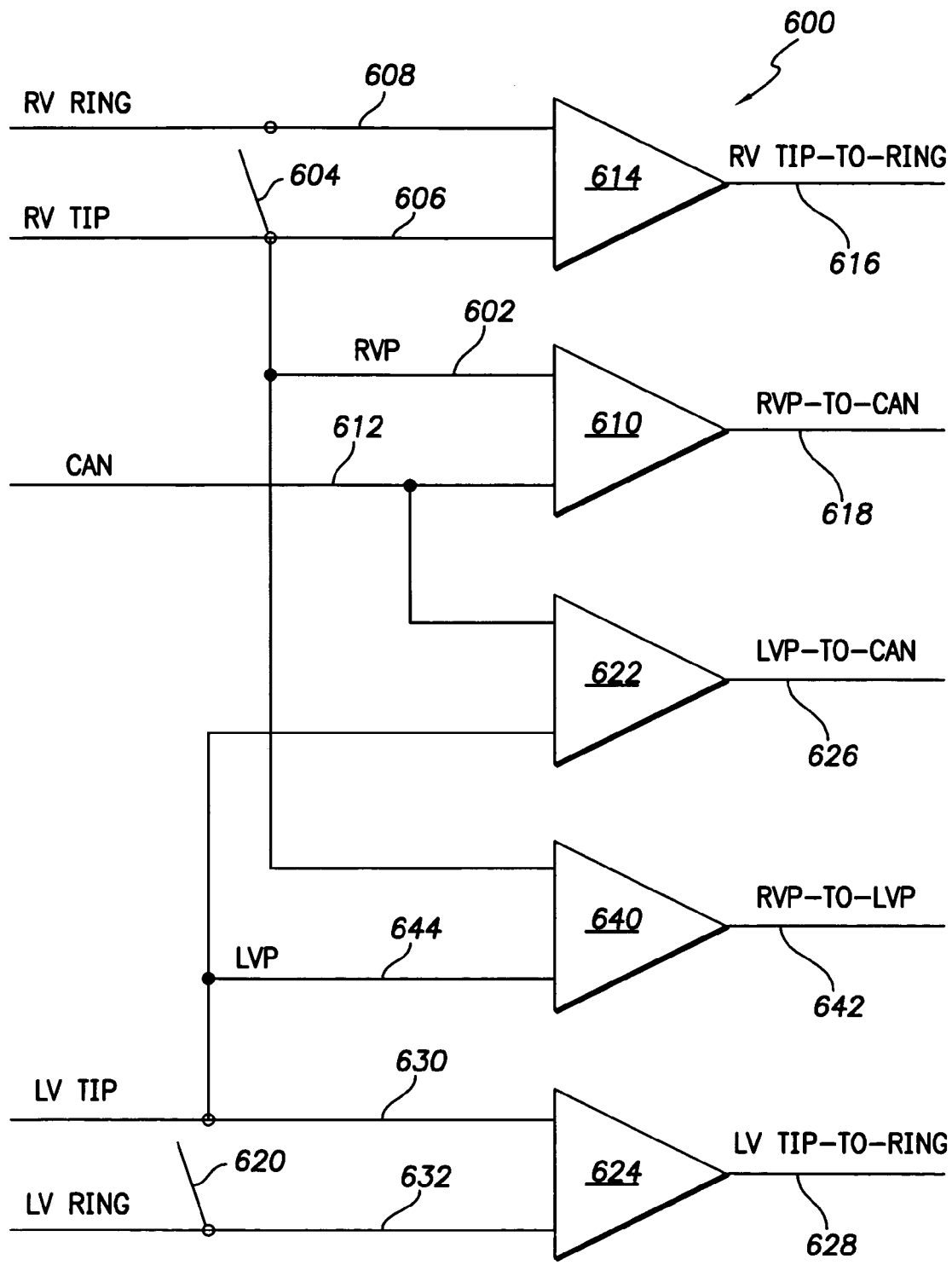
FIG. 6 is a simplified diagram of one embodiment of sensing circuitry constructed in accordance with the invention.

In some embodiments signals from the ventricle tip and ring electrodes are combined to simulate a larger electrode. For example, FIG. 6 depicts a circuit 600 that generates a right ventricle parallel tip-ring ("RVP") signal on a lead 602 when a switch 604 is closed. Specifically, the switch shorts a right ventricle tip lead 606 (e.g., from terminal 212, FIG. 2) to a right ventricle ring lead 608 (e.g., from terminal 214, FIG. 2). A sense circuit 610 references the resulting RVP signal on lead 602 to a can lead 612 to provide an RVP-to-can signal on lead 618.

The circuit 600 may be used to switch from a normal mode of sensing to a global mode of sensing. In the normal mode, the switch 604 is open and a sense circuit 614 generates a bipolar right ventricle tip-to-ring signal on lead 616. When the switch 604 is closed the circuit 600 generates the global RVP-to-can signal on lead 618.

In this same situation, the mode of response to a sensed signal changes. In the normal mode of response, the sensed or detected signal causes the stimulation device to inhibit its output. When the sensing configuration changes in response to a detected atrial tachyarrhythmia, the response also changes such that the early detected response causes the system to deliver or trigger a stimulus to one or more electrodes in the ventricle.

In a similar manner a switch 620 and sense circuits 622 and 624 may generate an LVP-to-can signal on lead 626 and a left ventricle tip-to-ring signal on lead 628, respectively, from the left ventricle tip and ring signals on leads 630 and 632. In this case, the global signal may comprise the LVP-to-can signal.

Some embodiments generate a global signal using a bipolar electrode configuration. For example, the sense circuit 640 may generate an RVP-to-LVP signal on lead 642 when the switches 602 and 620 are closed thereby providing RVP on lead 602 and LVP on lead 644. Alternatively, sense circuit 640 may generate a right ventricle tip to left ventricle tip signal on lead 642 when the switches 602 and 620 are open. Other signal combinations are readily apparent from the diagram. FIG. 5 illustrates a simplified example of a field pattern 504 that represents an area within which a bipolar right ventricle to left ventricle electrode configuration may sense signals.

Signals such as those discussed above in conjunction with FIG. 6 may be combined in a variety of other ways. For example, signals may be combined using one or more switches in the implantable leads. Alternatively, signals may be combined after they are sensed by the sense circuits.

In some embodiments a change in the mode of sensing involves selection of specific filters or filter characteristics. For example, to effectively detect ventricular activation a filter may need to pass lower frequency and/or lower amplitude signals as compared to other modes of sensing. Hence, the stimulation device 100 may select a filter with a wider pass band or a lower frequency pass band.

Thus, during a switch from a normal mode of sensing (e.g., ventricle tip-to-ring) to a global mode of sensing (e.g., ventricle tip-to-can), the stimulation device 100 may need to switch from one input filter or filter characteristic (e.g., relatively narrow bandwidth) to a different input filter or filter characteristic (e.g., wider bandwidth). This switch may be accomplished in a variety of ways depending on the type of filter.

In various embodiments, a filter may be implemented as a discrete filter or implemented using a filter application program that performs filter processing on digitized signals. Accordingly, selecting a filter may involve switching discrete filter into or out of a signal path. Alternatively, selecting a filter may involve selecting a different filter application program. Either of these type of filters may be an adjustable filter. In this case, the stimulation device may simply alter the characteristics of the filter by, for example, providing different input signals to a discrete filter or by providing different configuration inputs to a filter application program.

Referring again to FIG. 3, in some embodiments the stimulation device 100 may change its mode of pacing so that it may pace the ventricles in an effective manner during atrial tachyarrhythmia. For example, as represented by blocks 318 and 320, the stimulation device may pace the heart by detecting ventricular activation then stimulating the right and left ventricles.

The detection process of block 318 involves processing the sensed signals to determine whether a sensed signal corresponds to ventricular activation. This processing may involve analog and/or digital signals and may include, for example, comparison and/or analysis of characteristics of these signals.

Since the desired ventricle signal may have relatively small amplitude several techniques may be employed to accurately detect this signal. For example, the voltage threshold for the cutoff may be raised.

In some embodiments, the stimulation device 100 runs tests on the sensed signals to verify whether they are ventricular activation signals by, for example, comparing the signals with other sensed signals. This may involve repetitively sensing, over several beat periods, a set of signals generated during each beat period. Based on this analysis, one of the signals in the set may then be characterized as a ventricular activation signal. For example, ventricular activation may precede ventricular contraction by a relatively consistent period of time under given conditions. By verifying that the delay between a suspected ventricular activation signal and ventricular contraction is of the expected magnitude and by verifying that the time delay between these signals is relatively consistent over time, the stimulation device 100 may confirm that the suspected signal is a ventricular activation signal.

In some embodiments, mechanical ventricular contraction may be identified during these tests using an appropriate sensor or sensors. For example, an acceleration sensor such as an endocardial accelerometer or an epicardial accelerometer capable of detecting peak endocardial acceleration may be used to detect mechanical contraction. Also, a pressure sensor that measures changes in pressure (dp/dt) may be used to measure contraction in the heart chamber.

In one embodiment, after detection of atrial fibrillation, the stimulation device 100 parallels the right ventricle tip and ring as discussed above. This is accomplished by sending a command signal from the controller 220 to the switch 226. Here, the switch 226 includes a switch as discussed above in conjunction with FIG. 6. The paralleled tip and ring electrode provides an RVP signal that is comparable to a signal that may be generated by a larger electrode. As a result, the electrodes may sense further into the myocardium to sense more distance depolarizations. After the RVP signal is sensed the stimulation device 100 waits for up to 50 mS while detecting in a bipolar mode to verify that an electrical depolarization did go past the right ventricle. When a relatively consistent delay is observed between the start of the RVP signal and local activity (e.g., depolarization), the RVP signal may be characterized as the earliest onset of ventricular activation.

In addition, the stimulation device 100 may monitor other signals such as an atrial signal to verify that these other signals are not being incorrectly identified as ventricular activation by the global sense electrodes. This may be accomplished, for example, by comparing the relative timing and amplitudes of signals sensed by electrodes in the atria and in the ventricles.

U.S. Pat. No. 5,522,855 and U.S. patent application Ser. No. 10/728,459, filed Dec. 5, 2003, describe systems that incorporate unipolar atrial and ventricle leads that may be used to discriminate between atrial and ventricular events. Here, ventricular sensing may be provided using a Vtip to can electrode configuration and atrial sensing may be provided using a Vtip to Atip electrode configuration. A true ventricular complex would be detected on both channels (atrial and ventricle leads). On the other hand, during a true atrial complex, a true atrial signal would only be detected on the atrial channel and noise would be detected on the ventricle channel. Logic in the pacemaker discriminates between the complexes.

In some embodiments, more than one sensor may sense ventricular activation. In this case, the stimulation device 100 may compare these signals to determine which sensor provides the earliest indication of ventricular activation. The stimulation device 100 may then use this sensor for sensing ventricular activation. For example, in one embodiment both the RVP-to-can signal and the LVP-to-can signal may be sensed during a test procedure. The test procedure will determine which of the two signals provides the earliest indication. The stimulation device 100 is then configured so that during operation the stimulation device 100 senses the signal that provides the earliest indication.

Referring to block 320 in FIG. 3, after ventricular activation is sensed, the stimulation device 100 applies stimulation signals to one or both of the ventricles. Typically, stimulation is started immediately after ventricular activation is detected.

In some embodiments, stimulation is applied to both ventricles simultaneously. In this case, regardless of which ventricle was first activated, stimulation may be applied to a ventricle that has not been activated. Thus, in these embodiments detection of atrial tachyarrhythmia may result in a change in the timing between pacing of the left and right ventricles. For example, this time may change from the delay discussed above in conjunction with block 310 to essentially no delay.

Other forms of pacing may be used at block 320. For example, if ventricular activation is first detected in one of the ventricles, stimulation may be applied only to the other ventricle.

If a ventricular activation signal is not detected within a defined period of time, timers in the stimulation device 100 will "timeout" and the stimulation device 100 will pace the ventricles. Typically, this pacing will be performed in the same manner as is done when a timeout occurs during a normal mode of operation.

In general, the detecting and pacing operations described above may incorporate conventional techniques and may be implemented using conventional leads, sensors, hardware and software. For example, the ventricles may be paced using leads as described above in conjunction with FIG. 2.

Figure 7:
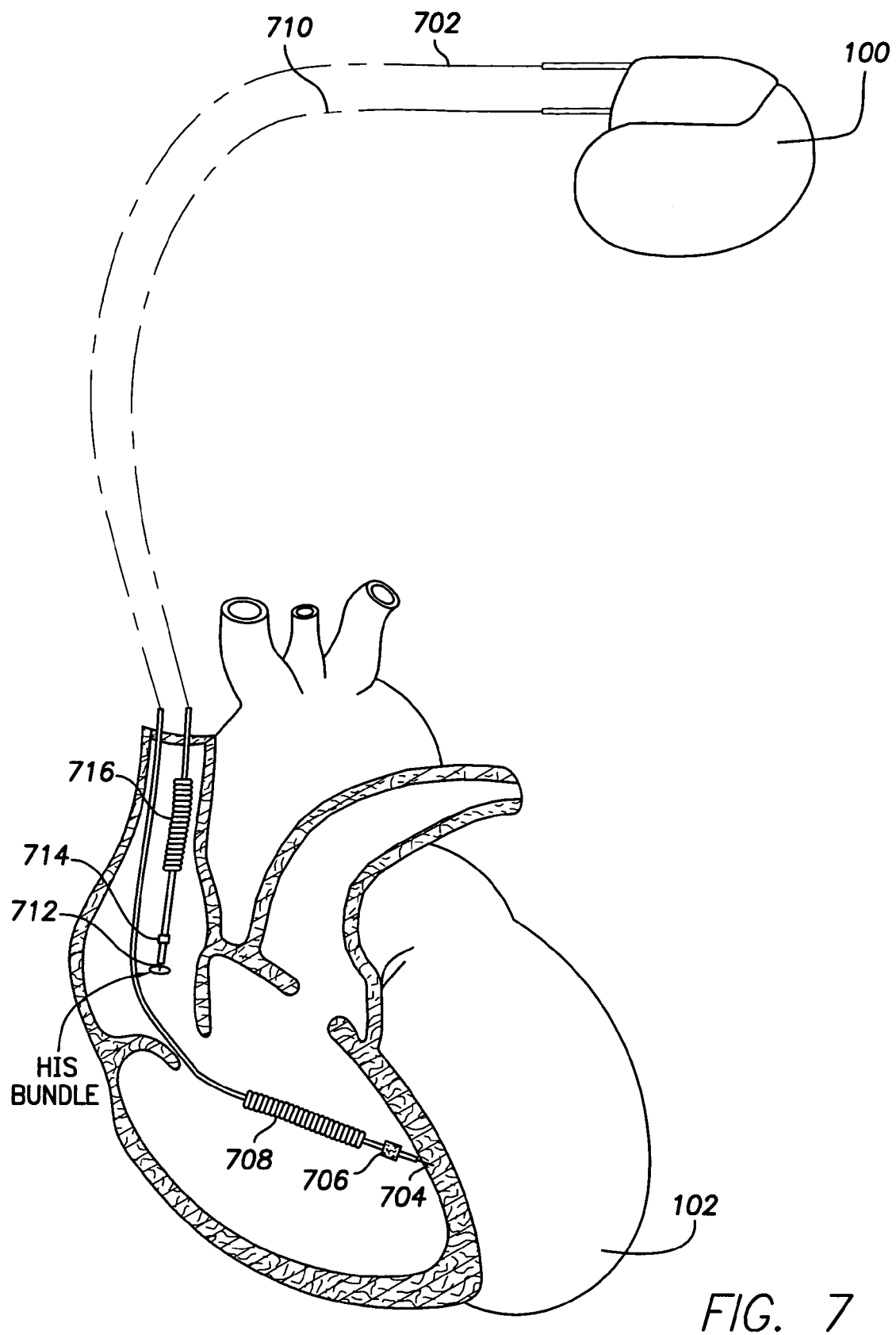
FIG. 7 is a simplified diagram of one embodiment of an implantable stimulation device in electrical communication with a lead implanted into a patient's heart for sensing precursor signals in accordance with the invention.
Figure 8:
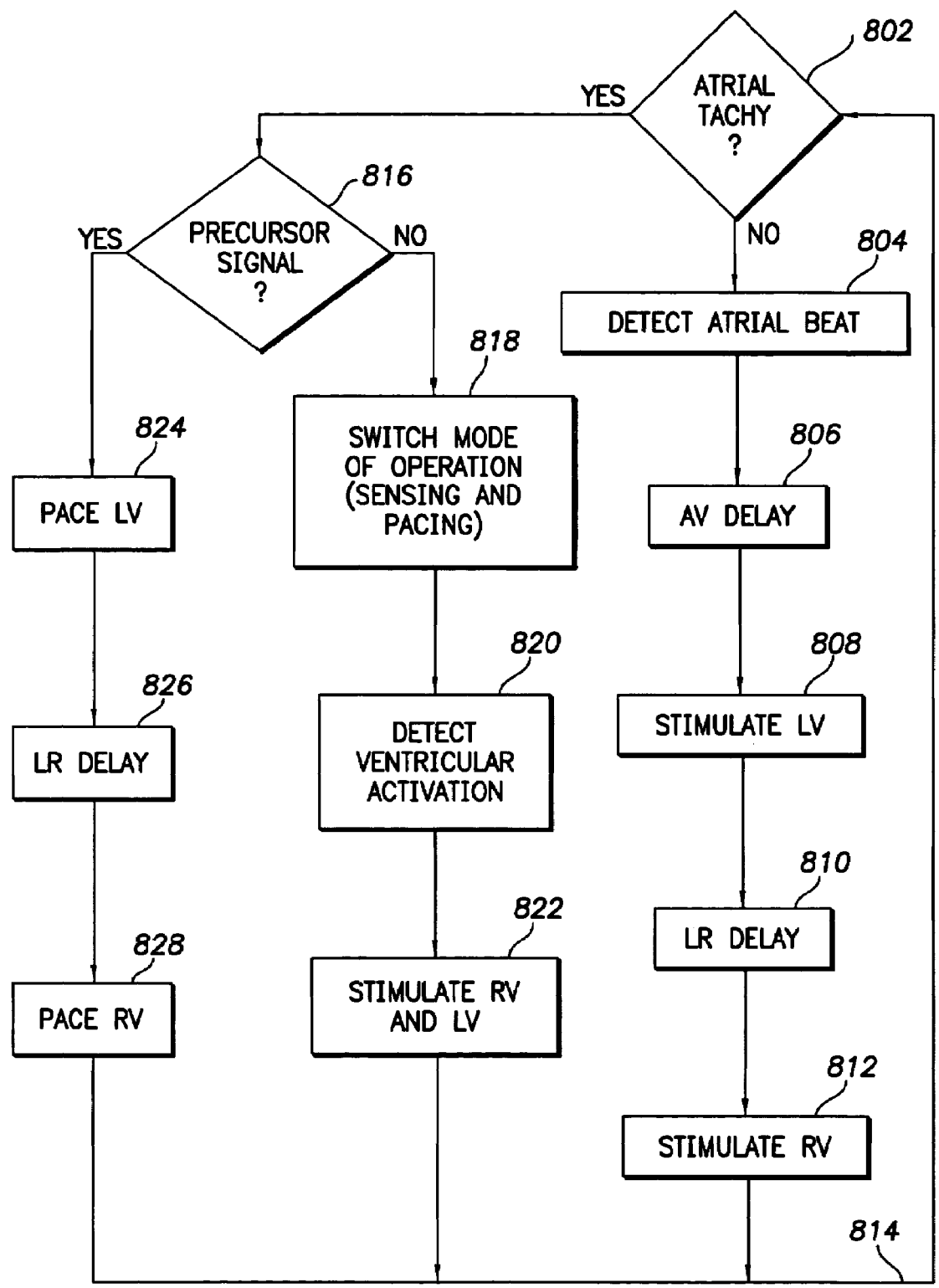
FIG. 8 is a simplified flow chart of one embodiment of operations that may be performed in accordance with the invention.

FIGS. 7 and 8 relate to an embodiment of a stimulation device that triggers ventricle stimulation off of signals that are precursors to ventricular activation. Such precursor signals include for example a signal from the bundle of His or a signal from an upper portion of the septum.

FIG. 7 is a simplified diagram that illustrates a lead 702 that may be used to sense a signal from the interventricular septum. The lead 702 may be transvenously inserted into the heart in a manner similar to the insertion of the right ventricle lead 108 discussed above in conjunction with FIG. 2. The lead 702 may be constructed of conventional lead materials using conventional techniques. For example, as depicted in FIG. 7, this lead may include bipolar tip and ring electrodes 704 and 706 and a coil electrode 708.

Similarly, a His lead 710 positioned in the proximity of the bundle of His may be used to sense signals from the bundle of His. The His lead 710 may include, for example, a His electrode 712, a His ring electrode 714 and a His coil electrode 716. This lead may be positioned and attached to the heart using conventional leads (e.g., a bipolar pair electrode) and techniques that may be used, for example, during a heart analysis stage or stimulation device implant stage for a patient. Known techniques also may be applied to ensure that this lead may be attached to the heart on a long term basis and that the lead is not too invasive in the area of attachment. Additional details relating to sensing the bundle of His are discussed, for example, in U.S. Pat. No. 6,609,027, the disclosure of which is hereby incorporated by reference herein.

The tip and ring electrodes (e.g., electrodes 704 and 706 or electrodes 712 and 714) for the precursor signals attach to the stimulation device 100 via terminals 211 and 213, respectively (FIG. 2). The stimulation device 100 also includes a precursor sense circuit 253 (FIG. 2) for amplifying and processing the precursor signals. The sense circuit 253 may be constructed in a manner similar to the other sense circuits discussed herein.

FIG. 8 is a flowchart 800 illustrating one embodiment of operations that may be performed by the stimulation device 100 when a precursor signal is available. The operations represented by blocks 802-812 and 818-822 correspond to the operations represented by blocks 302-312 and 316-320 in FIG. 3, respectively. Thus, when atrial tachyarrhythmia is not detected the stimulation device 100 provides normal pacing as represent by blocks 804-812.

As represented by block 816, when atrial tachyarrhythmia is detected the stimulation device 100 determines whether a precursor signal (e.g., bundle of His or septum signal) is present. This may involve, for example, checking a status flag that is set when the associated precursor lead is installed. Setting the status flag also may involve repetitively checking the precursor signals received from the precursor lead to determine whether reliable signals are being received. If a precursor signal is not present the operations of blocks 818-822 are performed as discussed above.

If at block 816 the precursor signal is present the stimulation device paces (e.g., stimulates) the left ventricle (block 824). This stimulation may be applied after a defined delay period. Preferably, this stimulation will be applied before ventricular activation commences as a result of the propagation of the sensed precursor signal to the ventricles. For example, the normal delay between a bundle of His signal and ventricular activation may be on the order 40-55 mS. The bundle of His to ventricular activation conduction time is longer for patients undergoing CRT for congestive heart failure and underlying LBBB. In either case, the delay between sensing the precursor signal and pacing the left ventricle is preferably shorter than the His signal to activation delay.

As represented by block 826, the stimulation device 100 may then delay a defined period of time. For example, this delay period may correspond to the normal delay between activation of the left and right ventricles in a healthy patient under given conditions.

As represented by block 828, the stimulation device 100 then paces the right ventricle. The process may then be repeated for the next beat as represented by line 814.

It should be appreciated that other methods of pacing one or more of the ventricles or multiple sites within a ventricle may be implemented in place of the operations described above.

In general, the pacing operations described above may be implemented using conventional techniques and conventional leads, hardware and software. For example, the ventricles may be paced using leads as described above in conjunction with FIG. 2.

Figure 9:
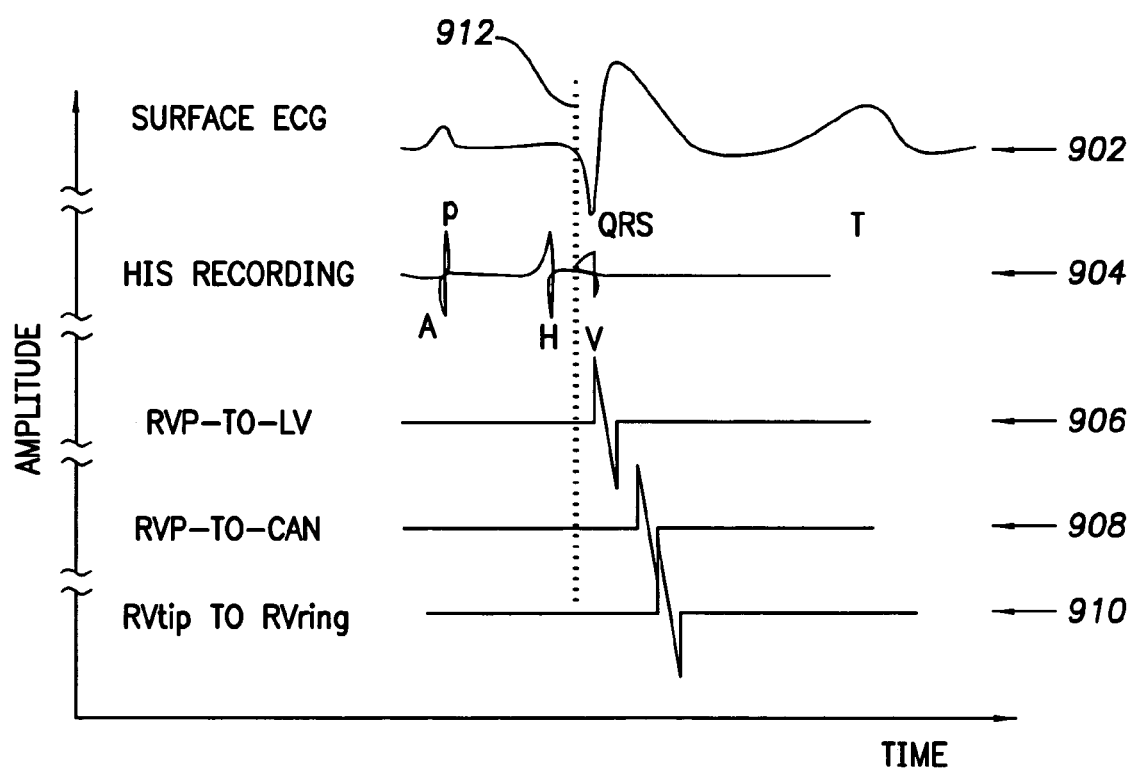
FIG. 9 is a schematic diagram depicting one example of signals associated with the ventricles and the bundle of His.

FIG. 9 depicts simplified schematic examples of several signals that may be sensed according to the teachings herein. The x axis denotes a time line and the y axis denotes the amplitude of the signals. For convenience all of the signals have been combined on a single graph. As a result, the y axis is broken into segments to show the amplitude of each signal.

The first signal 902 is a surface ECG signal and illustrates the P, QRS and T wave sequence. The onset of ventricular activity is represented by the vertical dashed line 912. The second signal 904 is a bundle of His signal. As illustrated, the His bundle signal 906 precedes the ventricle activation signals and may be shorter in length and lower in amplitude as compared to the ventricle signals 906, 908 and 908 depicted in FIG. 9.

The three ventricle signals 906, 908 and 908 may have relatively similar waveforms as represented by the simplified waveforms in FIG. 9. However, due to differences in the methods of sensing, the signals may provide an indication of ventricular activation at different times and in different areas of the ventricle. The third signal 906 is an RVP to left ventricle tip electrode signal. The form of this signal may be relatively similar to a "skin surface" ECG signal. This results, in part, from the use of a relatively large effective electrode provided by the paralleled tip and ring electrodes. The fourth signal 908 is an RVP to can signal. The characteristics of this signal are relatively similar to those of the third signal 906 as it also uses RVP. However, ventricular activation may be indicated later using this signal. The fifth signal 910 is an RV tip to RV ring signal. Ventricular activation may be indicated even later using this signal.

The teachings herein may be applied in conjunction with a variety of other treatments procedures. For example, in some embodiments, upon detection of atrial fibrillation the stimulation device may mode switch to revert to a non-tracking mode, at least with respect to atrial activity, and increase the base rate. This embodiment may be used to stabilize ventricular response via concealed retrograde conduction.

Another embodiment may incorporate dynamic ventricular overdrive ("DVO") in an attempt to stabilize the ventricular rate when it is irregular in response to the native atrial tachyarrhythmia with variable AV nodal conduction. Here, for fully paced beats, standard biventricular stimulation may be used while the sensed beats would trigger ventricular stimulation at a slightly faster rate. The objective of the slightly faster rate in accord with DVO would be to regularize and control the ventricular response by blocking anterograde AV nodal conduction by way of concealed retrograde conduction into the AV node rendering it physiologically refractory helping to block anterograde conduction. This may provide some degree of cardiac resynchronization therapy for the native beats. However, this procedure may not be as good as pure biventricular pacing as one chamber may have already started to depolarize. Nevertheless, the use of DVO may help stabilize the rhythm of the heart thereby improving the effectiveness of some of the techniques discussed. This may, in turn, provide an improvement in overall therapy for the patient.

The teachings herein may be applied to any patient in need of ventricular pacing who has some degree of signal conduction through the A-V node. Hence, applications are not limited to those patients with congestive heart failure such as a bundle branch block. For example, the teachings herein may prove beneficial for patients who have relatively good ventricles.

Different embodiments of the stimulation device may include a variety of hardware and software processing components. In some embodiments of the invention, hardware components such as controllers, state machines and/or logic are used in a system constructed in accordance with the invention. In some embodiments, code such as software or firmware executing on one or more processing devices may be used to implement one or more of the described operations.

The components and functions described herein may be connected/coupled in many different ways. The manner in which this is done may depend, in part, on whether and how the components are separated from the other components. In some embodiments some of the connections/couplings represented by the lead lines in the drawings may be in an integrated circuit, on a circuit board or implemented as discrete wires.

The signals discussed herein may take several forms. For example, in some embodiments a signal may be an electrical signal transmitted over a wire while other signals may consist of wireless signals transmitted trough space. In addition, a group of signals may be collectively referred to as a signal herein.

The signals discussed above also may take the form of data. For example, in some embodiments an application program may send a signal to another application program. Such a signal may be stored in a data memory.

In summary, the invention described herein generally relates to an improved cardiac pacing apparatus and method. While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of systems and processes. It will thus be recognized that various modifications may be made to the illustrated and other embodiments of the invention described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. An implantable cardiac stimulation system comprising:
   at least one atrial tachyarrhythmia detection circuit adapted to detect atrial tachyarrhythmias;
   at least one cardiac sensing circuit configured to sense cardiac electrical signals using a plurality of different ventricular sensing vectors,
   at least one pacing circuit configured to pace at least one ventricle in accordance with a plurality of modes of pacing; and
   wherein the at least one atrial tachyarrhythmia detection circuit is configured to select a first one of the plurality of ventricular sensing vectors and a first one of the modes of pacing during a normal mode of operation and to select a second one of the plurality of ventricular sensing vectors and a second one of the modes of pacing in response to the detection of an atrial tachyarrhythmia.

2. The system of claim 1 wherein, in accordance with a selected mode of sensing, the at least one cardiac sensing circuit senses onset of ventricular activation.

3. The system of claim 2 wherein, in accordance with a selected mode of pacing, the at least one pacing circuit paces the at least one ventricle in response to sensing the onset of ventricular activation.

4. The system of claim 2 wherein, in accordance with a selected mode of pacing, the at least one pacing circuit simultaneously paces multiple sites in at least one of the ventricles in response to sensing the onset of ventricular activation.

5. The system of claim 1 wherein, in accordance with a selected mode of pacing, the at least one pacing circuit simultaneously paces both ventricles.

6. The system of claim 1 wherein the at least one cardiac sensing circuit comprises at least one lead for sensing a bundle of His signal.

7. The system of claim 1 wherein the at least one cardiac sensing circuit comprises at least one lead for sensing a septum signal.

8. The system of claim 1 wherein the at least one cardiac sensing circuit comprises at least one lead for sensing a global signal.

9. The system of claim 1 wherein, in accordance with a selected mode of pacing, the at least one pacing circuit changes ventricle to ventricle pacing timing.

10. The system of claim 1 wherein the at least one cardiac sensing circuit comprises at least one lead for sensing substantially within a first area in accordance with a first mode of sensing or sensing substantially within a second area in accordance with a selected mode of pacing, wherein the second area is different than the first area.

11. The system of claim 1 wherein the at least one cardiac sensing circuit comprises:
   a plurality of leads positioned a first distance apart for sensing in accordance with a first mode of sensing; and
   a plurality of leads positioned a second distance apart for sensing in accordance with a selected mode of sensing in response to the detection of an atrial arrhythmia, wherein the second distance is larger than the first distance.

12. The system of claim 1 wherein the at least one cardiac sensing circuit comprises at least one lead for sensing a bipolar signal in accordance with a first mode of sensing and for sensing a unipolar signal in accordance with a selected mode of sensing in response to the detection of an atrial arrhythmia.

13. The system of claim 1 wherein the at least one cardiac sensing circuit comprises:
   at least one bipolar electrode for sensing in accordance with a first mode of sensing; and
   at least one electrode for sensing in accordance with a selected global mode of sensing in response to the detection of an atrial arrhythmia.

14. The system of claim 1 wherein the at least one cardiac sensing circuit comprises at least one lead for sensing a right ventricle tip-to-ring signal in accordance with a first mode of sensing and for sensing a right ventricle tip-to-can signal in accordance with a selected mode of sensing in response to the detection of an atrial arrhythmia.

15. The system of claim 1 wherein the at least one cardiac sensing circuit comprises at least one lead for sensing a paralleled tip and ring signal in accordance with a selected mode of sensing in response to the detection of an atrial arrhythmia.

16. The system of claim 1 comprising at least one filter wherein a first mode of sensing comprises sensing using a first filter characteristic and a selected mode of sensing in response to the detection of an atrial arrhythmia comprises sensing using a second filter characteristic, wherein the second filter characteristic is different than the first filter characteristic.

17. The system of claim 16 wherein the first filter characteristic comprises a first bandwidth and the second filter characteristic comprises a second bandwidth, wherein the second bandwidth is wider than the first bandwidth.

18. The system of claim 1 comprising at least one threshold detector wherein a first mode of sensing comprises sensing using a first amplitude threshold and a selected mode of sensing comprises sensing using a second amplitude threshold, wherein the first amplitude threshold is higher than the second amplitude threshold.

19. The system of claim 1 wherein the at least one atrial tachyarrhythmia detection circuit detects at least one of the group consisting of atrial fibrillation, atrial flutter and atrial tachycardia.

20. A system comprising:
- means for interacting with at least one ventricle of a heart in accordance with a first mode of pacing and a first ventricular sensing vector;
- means for detecting an atrial tachyarrhythmia; and
- means for switching to a second mode of pacing and a second ventricular sensing vector in response to detection of the atrial tachyarrhythmia.

* * * * *